United States Patent [19]

Berman

[11] Patent Number: 5,458,635
[45] Date of Patent: Oct. 17, 1995

[54] BREAST FORM

[76] Inventor: Miriam B. Berman, 4300 N. Ocean Blvd., Apt. PH-E, Fort Lauderdale, Fla. 33308

[21] Appl. No.: 167,136

[22] Filed: Dec. 16, 1993

[51] Int. Cl.⁶ .................................. A61F 2/12; A61F 2/52
[52] U.S. Cl. ........................................................ 623/8; 623/7
[58] Field of Search ..................... 623/7, 8, 11; 264/222, 264/DIG. 30

[56] References Cited

U.S. PATENT DOCUMENTS

| | | | |
|---|---|---|---|
| 2,258,209 | 10/1941 | De Jorio | 128/282 |
| 2,814,808 | 12/1957 | Berman | 623/7 |
| 3,278,947 | 10/1966 | Silverman | 3/36 |
| 3,514,792 | 6/1970 | Freedman | 3/36 |
| 3,706,104 | 12/1972 | Dehlin et al. | 3/36 |
| 3,811,133 | 5/1974 | Harris | 3/36 |
| 3,858,248 | 1/1975 | Crowe | 3/36 |
| 3,896,506 | 7/1975 | Hankin et al. | 3/36 |
| 3,950,792 | 4/1976 | Williams | 623/7 |
| 4,019,209 | 4/1977 | Spence | 128/481 |
| 4,023,575 | 5/1977 | Nixon | 128/481 |
| 4,024,856 | 5/1977 | Kirianoff | 128/2 |
| 4,024,876 | 5/1977 | Silverman | 3/36 |
| 4,071,914 | 2/1978 | Silverman | 3/36 |
| 4,086,666 | 5/1978 | Vaskys et al. | 3/36 |
| 4,125,117 | 11/1978 | Lee | 128/481 |
| 4,185,332 | 1/1980 | Jahnig | 623/7 |
| 4,199,825 | 4/1980 | Knoche | 3/36 |
| 4,356,573 | 11/1982 | Knoche | 623/7 |
| 4,401,492 | 8/1983 | Pfommer | 156/71 |
| 4,701,230 | 10/1987 | Loi | 156/145 |
| 4,828,559 | 5/1989 | Greenberg | 623/7 |
| 5,066,302 | 11/1991 | Rice | 623/7 |
| 5,340,352 | 8/1994 | Nakanishi et al. | 623/7 |

FOREIGN PATENT DOCUMENTS

| | | |
|---|---|---|
| 1406005 | 6/1965 | France . |
| 1072358 | 12/1959 | Germany . |
| 2802376 | 7/1979 | Germany . |

OTHER PUBLICATIONS

Ser. No. 4,249,975 Feb. 1981 Brochure of Amoena Corporation.

*Primary Examiner*—Debra S. Brittingham
*Attorney, Agent, or Firm*—Oltman and Flynn

[57] ABSTRACT

An artificial breast form is disclosed which includes contoured, molded breast shape layers that can be sculptured by the user to create a cosmetically acceptable appearance. The artificial breast form package for insertion between a brassiere and a breast comprises a cover with adhesive nylon tape surface to adhere to the inner cup of the brassiere, an external molded layer abutting against the cover, an internal molded layer abutting against the external molded layer, and a back molded layer located between the internal layer and a breast. The cover can include lace trim or a picot edge. The cover can be one of stretch lace, stretch sheer, stretch matte jersey or stretch cotton knit. cover The external molded layer, the internal molded layer and the back layer are formed from any one of polyurethane, silicone and foam rubber. The external molded layer can be a wafer layer sculpted in the shape of a breast with an optional side flange. The internal molded layer can be at least one wafer contour layer contoured to fit flush against the back layer and the external layer. The back molded layer can be a wafer contour layer heavier and more dense than the internal and external layers sculpted to resemble the breast of the user. An optional insert cover(s) with adhesive nylon surface can be used with internal molded layers if the internal molded layers are to be used by themselves within a brassiere. A method of making an artificial breast form package is also disclosed which comprises molding an external layer with optional side flange to resemble the contour of the front of a breast, molding an internal layer contoured to fit flush against the the external layer, molding a back layer to be heavier and more dense than the internal and external layers and sculpted to resemble the breast of the user, and curing each layer. The type of molding can include injection molding. The external, internal and back layers can be molded from either polyurethane, silicone or foam rubber.

16 Claims, 3 Drawing Sheets

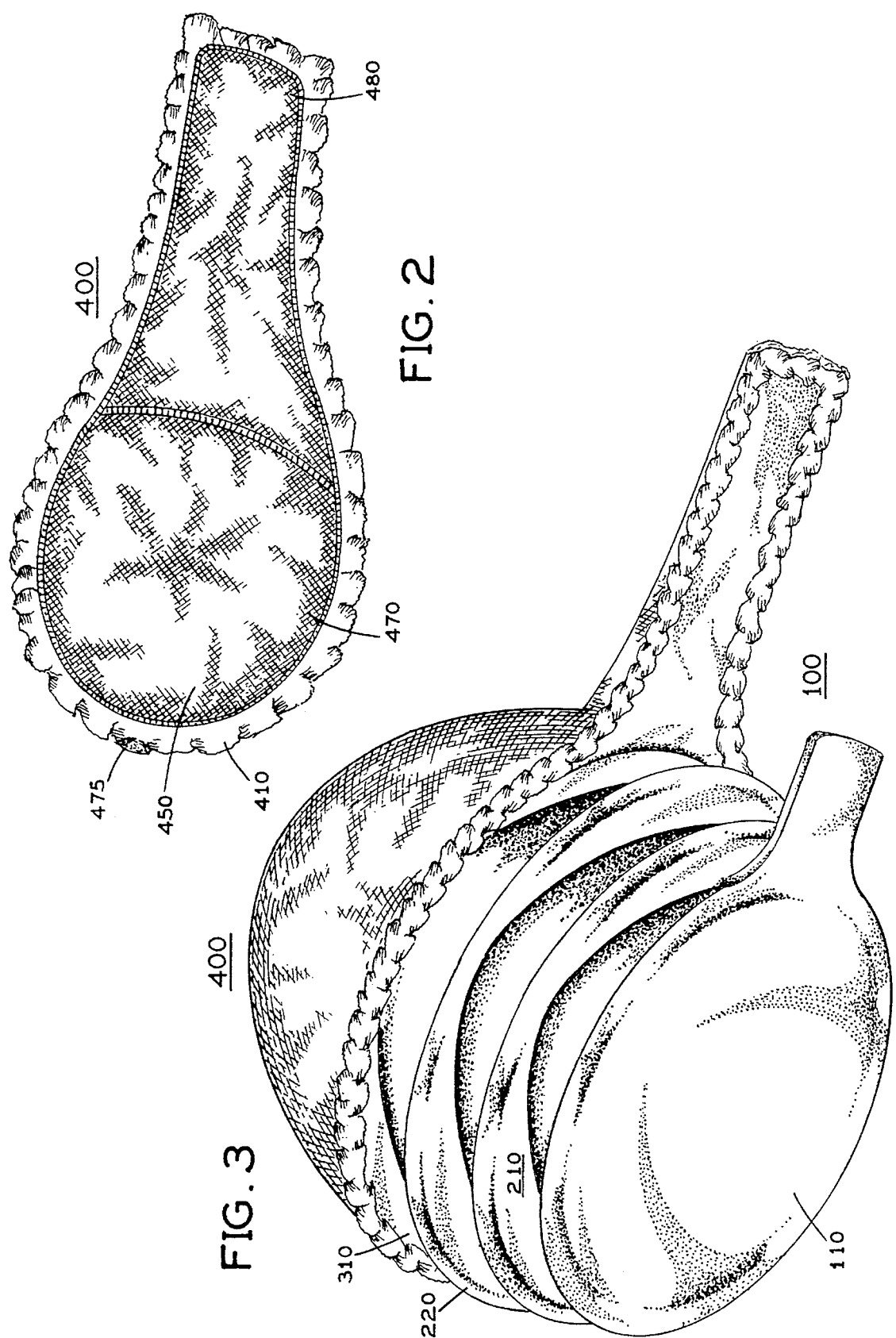

BREAST FORM

This invention relates to artificial breast forms, and in particular to contoured, molded breast shape layers that can be sculptured by the user to create a cosmetically acceptable appearance.

BACKGROUND AND PRIOR ART

Mastectomy patients have looked toward artificial breast forms as a substitute for the removed breast tissue. Many of these forms have been heavy, bulky and uncomfortable to the user. Further, many of these forms ride up in a brassiere to form uneven and unnatural appearances. Further, many of theses forms are composed of materials such as sand that does not feel natural to the touch. Also, many forms require custom fitting that can be expensive to individually manufacture.

Breast implantation surgery for silicon and saline implantations have also had many problems such as but not limited to leakage that may require further surgery to remove the implant. Implantation methods are usually an expensive type of surgery and out of the reach of many people.

Thus, there is a need for a type of breast form that does not require surgery, nor is expensive nor requires a custom fitting by others.

SUMMARY OF THE INVENTION

The first objective of the present invention is to provide a non-surgical breast form that can be sculptured by the user to appear natural in appearance and touch.

The second object of this invention is to provide a breast form that allows the user to add or delete wafer like molded layers to achieve the cosmetically desired result.

The third object of this invention is to provide a breast form that does not feel heavy nor bulky toward the user.

The fourth object of this invention is to provide a breast form that can be used with an existing brassiere and does not require extra straps and support means.

The fifth object of the invention is to provide a breast form that can be mass produced and not prohibitive in price toward the user.

An artificial breast form is disclosed which includes contoured, molded breast shape layers that can be sculptured by the user to create a cosmetically acceptable appearance. The artificial breast form package which is inserted between a brassiere and a breast comprises a cover for positioning adjacent to the brassiere, an external molded layer abutting against the cover, an internal molded layer abutting against the external molded layer, and a back molded layer located between the internal layer and a breast. The cover can include lace trim or a picot edge. The cover can be stretch lace, stretch sheer, stretch matte jersey or stretch cotton knit. The cover can further include an adhesive tape surface and have a pocket back opening so that layer(s) can be held in place. The external molded layer, the internal molded layer and the back layer can be formed from polyurethane, silicone, foam rubber and the like. The external molded layer can be a layer sculpted in the shape of a breast with an optional side flange. The internal molded layer can be at least one contour layer contoured to fit flush against the back layer and the external layer. The back molded layer can be a contour layer heavier and more dense than the internal and external layers sculpted to resemble the breast of the user.

A method of making an artificial breast form package is also disclosed.

Further objects and advantages of this invention will be apparent from the following detailed description of a presently preferred embodiment which is illustrated schematically in the accompanying drawings.

BRIEF DESCRIPTION OF THE FIGURES

FIG. 2 shows a frontal view of the cover which can be used with the package of FIG. 1.

FIG. 3 illustrates an exploded view of the cover of FIG. 2 with the package of FIG. 1.

DESCRIPTION OF THE PREFERRED EMBODIMENT

Before explaining the disclosed embodiment of the present invention in detail it is to be understood that the invention is not limited in its application to the details of the particular arrangement shown since the invention is capable of other embodiments. Also, the terminology used herein is for the purpose of description and not of limitation.

Figure 1:
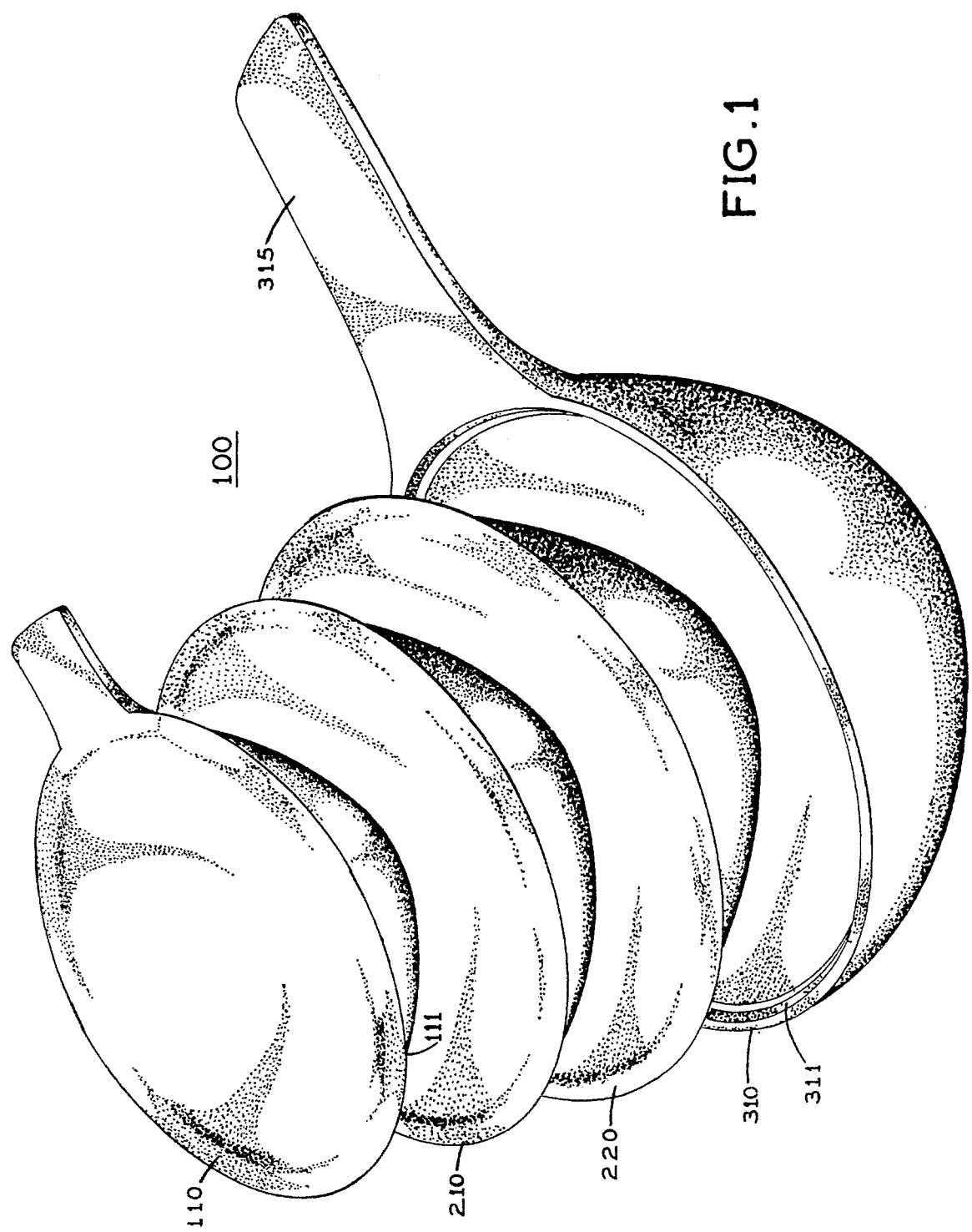
FIG. 1 illustrates an exploded view of the four molded layers of the artificial breast form package.

FIG. 1 illustrates an exploded view of the four molded layers of the artificial breast form package 100. The package can include a back molded layer 110 which is molded to fit over the user's breast, internal molded layer(s) 210 and 220 which fit over back molded layer 110, and an external molded layer 310 which fits over internal molded layers 210 and 220. The number of internal molded layers 210 and 220 can vary with the user's desires. External molded layer 310 can include an optional side flange 315.

The external molded layer 310, the internal molded layer(s) 210, 220 and the back layer 110 can be formed from polyurethane, silicone, foam rubber or any known combination thereof. Optimally, the layers will be flesh colored, natural feeling to the touch and have a natural motion.

External molded layer 310 can resemble the contour of the front of the breast to be normal in appearance, soft and natural to touch and light in weight. Internal molded layers 210 and 220 are contoured type fuller layers that can be thin and light to the touch. Back molded layer 110 can appear to resemble the contour and depth of the breast. Layer 110 can be firm to the touch, dense, and heavier in weight than the other layers. When all the layers are combined together, the rim 111 of back layer 110 abuts against the inner rim 311 of external molded layer 310. All the layers are intended to fit compactly into the adjacent one and separate apart in an effortless, simple manner.

FIG. 2 shows a frontal view of the cover 400 which can be used with the package 100 of FIG. 1. Cover 400 is intended to be a light weight stretch fabric that will be able to firmly accommodate the various layers and can include a pocket back opening in order for the layers to fit within. The cover 400 can have a trim 410 of either a lace or Picot edge. The cover material 450 can be made of stretch lace, stretch sheer, stretch matte jersey, stretch cotton knit or the like. Stretch matte jersey is a plain knitted fabric which can be made of nylon, wool, cotton or silk fiber or yarn. For the purposes of this invention it should be made of cotton. Stretch matte jersey is a close fitting knit, and it is safe and elastic. It is a fabric with a dull surface or dull finish. The cover 400 can include a adhesive tape such as the nylon hooks in Velcro TM or the like. The tape can run across the top surface 470 to enable the cover 400 to adhere to a brassiere or outer clothing being worn. Additionally there can be small pieces of adhesive tape located on the cover 400 near the point of cleavage 475 and near the armpit area 480 to prevent dislodgment when worn.

Figure 4:
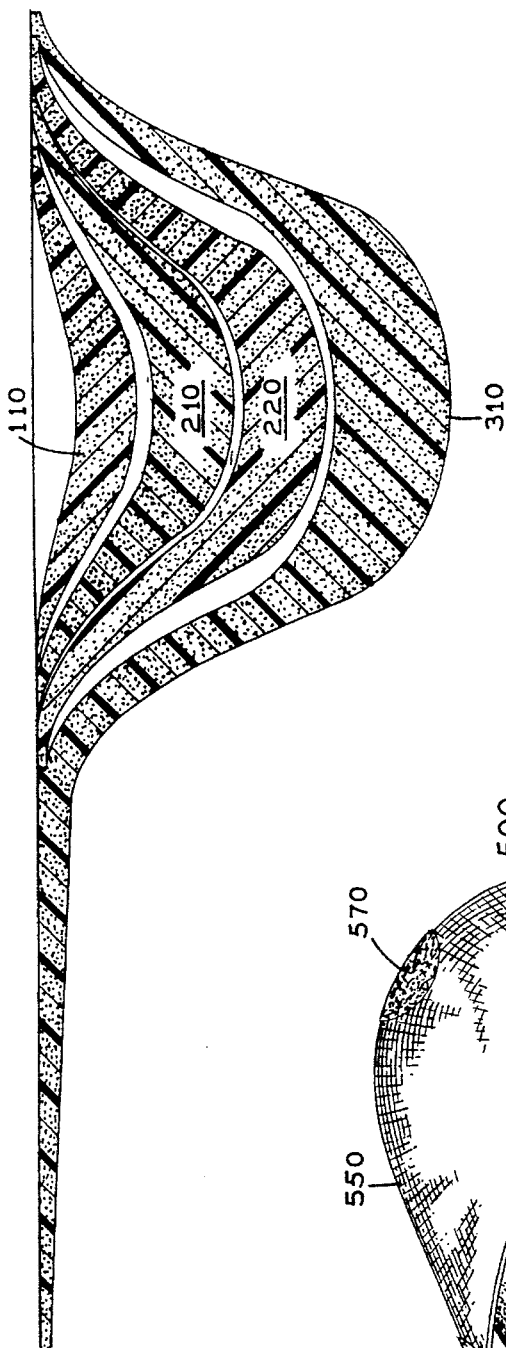
FIG. 4 illustrates a cut side view of the package of FIG. 1.

FIG. 3 illustrates an exploded view of the cover 400 of FIG. 2 with the package 100 of FIG. 1. FIG. 4 illustrates a cut side view of the package 100 of FIG. 1.

Figure 5:
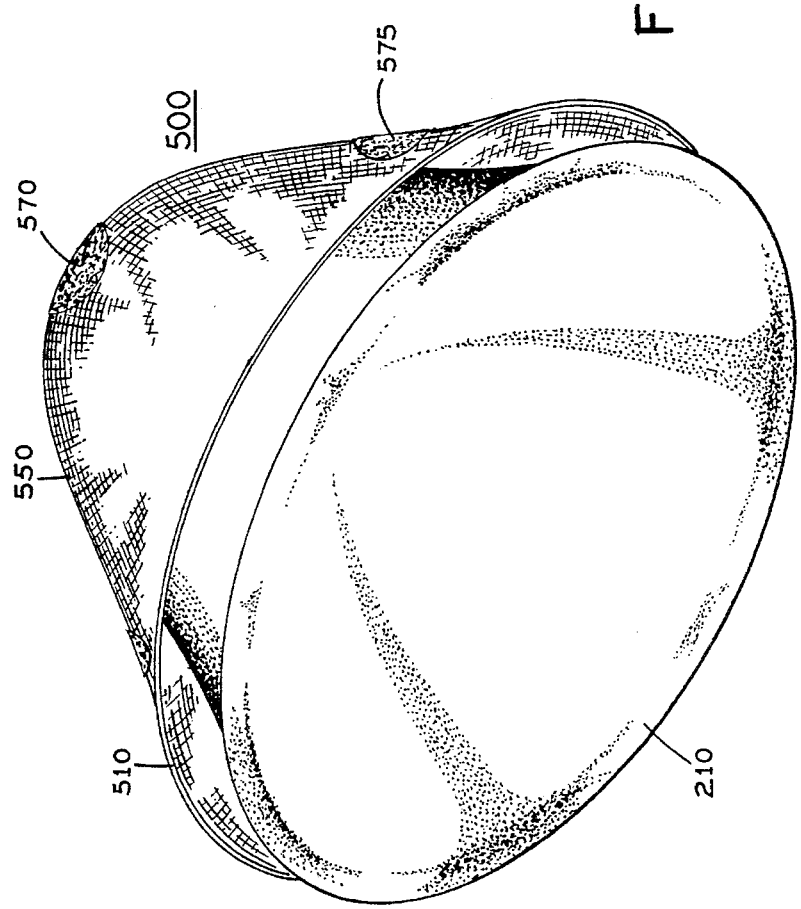
FIG. 5 shows an internal molded layer of FIG. 1 with an optional cover.

FIG. 5 shows an internal molded layer 210 of FIG. 1 with an optional cover 500. One can use one or more internal molded layers 210 and 220 by itself without back molded layer 110 or external molded layer 310. Similar to cover 400, cover 500 is intended to be a light weight stretch fabric that will be able to firmly accommodate the various layer or layers and can include a pocket back opening in order for the layers to fit within. Cover 500 can have a trim 510 of either a lace or Picot edge. The cover material 550 can be made of stretch lace, stretch sheer, stretch matte jersey, stretch cotton knit or the like. Cover 500 can include a adhesive tape such as the nylon hooks in Velcro TM or the like, across the top surface 570 to enable cover 500 to adhere to a brassiere or outer clothing being worn. Additionally there can be small pieces of adhesive tape located on the cover 500 near the point of cleavage 575.

A preferred method of using the package will now be discussed with reference to the above figures. Normally, the user is in the best position to shape an artificial breast form and not a doctor or manufacturer. With this invention the user can create and reconstruct the comfortable appearance that is desired. The user initially decides the number of internal molded layers 210 and 220 to be used. By deletion or addition of one or more of the internal molded layers 210 and 220, the user can create a cosmetically acceptable result. Internal molded layer(s) 210 and 220 are fit together and inserted between back molded layer 110 and external molded layer 310. The layers can be pliable enough to be sculptured by the user to create a cosmetically acceptable appearance.

These layers are then inserted into the back pocket area of cover 400. The layers and cover are then inserted between outer clothing such as a brassiere, and the breast area that is to be modified. The position of the components are adjusted by using the adhesive tape on the outer surface of the cover which can readily adhere to the outer clothing such as a bra.

The optional insert cover 500 with adhesive nylon surfaces 570 and 575 can be used with internal molded layers 210, 220 by themselves in a manner similar to the above description only without the back layer 110 nor the external layer 310.

METHOD OF MANUFACTURING

A method of making an artificial breast form package comprises molding an external layer with optional side flange to resemble the contour of the front of a breast, molding an internal layer contoured to fit flush against the the external layer, molding a back layer to be heavier and more dense than the internal and external layers and sculpted to resemble the breast of the user, and curing each layer. The type of molding can include injection molding. The external, internal and back layers can be molded from liquid forms of polyurethane, silicone, foam rubber or any known combination thereof. After injection into molds, the layers will be allowed to cure. After the cure step, the layers can be put together with other layers for use. Patterns made out of materials such as fiberglass, plastic or known combinations thereof can be used to determine the size of the layers to be used.

A cover is provided for the layers of the package, the cover will be die cut to fit the total sculpted, molded breast shape. Because of the nature of the stretch fabric it will be able to firmly accommodate the various parts of the sculptured molded Breast shape. The cover can include adhesive taped surfaces for adhesion to a bra.

The materials used and an object of manufacturing the invention is for being able to mass produce the breast form and to cream a breast prosthesis with a selling price that will not be prohibitive to users.

The sizes of each of the layers and covers can vary by bras and cup size as well as by the intent of the user. The layers and covers can be adapted for either or both the right or left breasts.

The package is not limited to being used only with brassieres. Both swimwear, strapless wear and other forms of clothing can be used with the molded layers. The package is not intended to be used only for surgery outpatients such who have undergone operations such as a mastectomy. People with normal breasts can readily use the invention to enhance one or both of their own breast sizes.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. An artificial breast form package for selective insertion between a brassiere and a breast comprising:

a discrete cover for removably positioning adjacent to the brassiere, a discrete external molded layer removably abutting against the cover, a discrete internal molded layer removably abutting against the external molded layer, and a discrete back molded layer removably positioned between the internal molded layer and the breast.

2. The artificial breast form package of claim 1, wherein the cover further includes:

stretch fabric with an adhesive tape surface and trim.

3. The artificial breast form package of claim 2, wherein the stretch fabric is selected from the group consisting of:

stretch lace, stretch sheer, stretch matte jersey and stretch cotton knit.

4. The artificial breast form package of claim 2, wherein the trim is selected from the group consisting of:

lace trim and a picot edge.

5. The artificial breast form package of claim 1, wherein the external molded layer, the internal molded layer and the back layer are formed from at least one material selected from the group consisting of:

polyurethane, silicone and foam rubber.

6. The artificial breast form package of claim 1, wherein the external molded layer further includes:

a layer sculpted in the shape of a breast.

7. The artificial breast form package of claim 6, wherein the external molded layer further includes:

a side flange.

8. An artificial breast form package of claim 1, wherein the internal molded layer further includes:

at least one contour layer contoured to fit flush against the back layer and the external layer.

9. An artificial breast form package of claim 1, wherein the back molded layer further includes:

a contour layer heavier and more dense than the internal and external layers sculpted to resemble the breast of the user.

10. An artificial breast form package comprising:

a discreet cover, a discreet external molded layer removably abutting against the cover, a discreet internal molded layer removably abutting against the external molded layer, and a discreet back molded layer removably positioned adjacent the internal molded layer.

11. The artificial breast form package of claim 10, wherein the cover further includes:

stretch fabric with an adhesive tape surface for attachment to brassiere, wherein the stretch fabric is selected from the group consisting of:

stretch lace, stretch sheer, stretch matte jersey and stretch cotton knit.

12. The artificial breast form package of claim 11, wherein the external molded layer, the internal molded layer and the back layer are formed from at least one material selected from the group consisting of:

polyurethane, silicone and foam rubber.

13. The artificial breast form package of claim 12, wherein the external molded layer further includes:

a layer sculpted in the shape of a breast.

14. The artificial breast form package of claim 13, wherein the external molded layer further includes:

a side flange.

15. An artificial breast form package of claim 14, wherein the internal molded layer further includes:

at least one contour layer contoured to fit flush against the back layer and the external layer.

16. An artificial breast form package of claim 15, wherein the back molded layer further includes:

a contour layer heavier and more dense than the internal and external layers sculpted to resemble the breast of the user.

* * * * *